United States Patent [19]

Hemsath

[11] Patent Number: 5,431,495

[45] Date of Patent: Jul. 11, 1995

[54] TEMPERATURE PROBE FOR DETERMINING CARBON SOOTING TEMPERATURES OF OIL MIXTURES ON STEEL STRIPS

[75] Inventor: Klaus H. Hemsath, Toledo, Ohio

[73] Assignee: Gas Research Institute, Chicago, Ill.

[21] Appl. No.: 208,712

[22] Filed: Mar. 11, 1994

[51] Int. Cl.⁶ .................. G01N 25/12; G01K 1/14; G01K 7/04; G01K 13/02

[52] U.S. Cl. .................. 374/15; 374/27; 374/148; 374/208; 374/166; 374/179; 374/16; 266/99; 266/100

[58] Field of Search .................. 374/27, 147, 148, 208, 374/166, 179, 16, 15; 266/99, 100

[56] References Cited

U.S. PATENT DOCUMENTS

| | | | |
|---|---|---|---|
| 3,130,584 | 4/1964 | Kennedy | 374/166 |
| 3,589,169 | 6/1971 | Lafitte et al. | 374/15 |
| 4,023,411 | 5/1977 | Escher | 374/147 |
| 5,064,506 | 11/1991 | Sparenberg et al. | 374/166 |
| 5,312,186 | 5/1994 | Swan | 374/147 |

Primary Examiner—Diego F. F. Gutierrez
Attorney, Agent, or Firm—Frank J. Nawalanic

[57] ABSTRACT

A temperature probe is disclosed for determining the temperature at which residual oils can be vaporized from cold rolled strip without producing free carbon. The probe includes an open ended first tubular member with a burner mounted at one end of the first tubular member for closing the end thereof so that the burner fires its products of combustion through the first tubular member and out the other end thereof. A closed end second tubular member concentrically receives the first tubular member to define an annular heat space therebetween and has an exhaust port in fluid communication with said annular heat space adjacent the burner. Insulation extends on the inside of the outer tubular member for a fixed distance thereof from the exhaust port and a water jacket adjacent the exhaust port provides a temperature gradient along the length of the tube coincident with the insulation to provide a steady state, temperature indicating device in which the temperature varies, as a gradient, along the length of the outer tube.

11 Claims, 3 Drawing Sheets

TEMPERATURE PROBE FOR DETERMINING CARBON SOOTING TEMPERATURES OF OIL MIXTURES ON STEEL STRIPS

This invention relates to a temperature probe for determining a specific temperature at which oily residues can be volatilized from cold rolled steel.

The invention has specific application for and will be described with particular reference to a batch coil annealing furnace in which oily residues are burned off the strip prior to annealing the coils. However, the invention in its broader sense, is not necessarily limited to batch coil annealing furnaces and can be used in other applications, such as in the rolling mill itself.

PRIOR ART

In cold rolling strip, the mill rolls leave a thin film of rolling oil residues on the strip which is not removed in the final cleaning operation before the strip is coiled or recoiled. Rolling oils are mixtures of petroleum derivatives, mineral oils, animal fats and other additives. Their composition varies. More importantly, for any given mill, the composition of the residue varies from coil to coil. When the coil is subjected to heat, the residues polymerize, pyrolize and form soot and carbon on the steel surfaces. The carbon fouls the surface resulting in poor paint adherence or poor adherence of any various coatings which might subsequently be applied to the strip.

Industry standards have not set forth a standardized procedure which will result in one boiling point or one sooting temperature or one coking temperature which can be set to volatilize the oil residual without carbon sooting or otherwise forming free carbon adhering to the strip surface.

SUMMARY OF THE INVENTION

Accordingly, it is a principal object of the invention to provide a temperature probe or steady state temperature indicating device which determines the temperature for any individual or specific coil at which the oil residuals can be volatilized without forming carbon soot This object along with other features of the invention is achieved by means of a temperature probe which includes an open ended first tubular member with a burner mounted at one end of the first tubular member and closing one end thereof so that the burner is adapted to fire its products of combustion through the first tubular member and out the opposite open end thereof. A closed end, second tubular member concentrically receives the first tubular member to define an annular heat space therebetween and the second tubular member has an exhaust port in fluid communication with the annular heat space at its first closed end which is adjacent the burner. An insulating arrangement extends a fixed distance along the inside of the second tubular member from its first closed end and prevents the hot burner products of combustion in the annular heat space from directly contacting the second tubular member along the fixed distance. A water jacket arrangement adjacent the first closed end of the second tubular member receives a cooling fluid for establishing a steady state, temperature gradient along the outside surface of the second tubular member over the fixed distance which gradient is used to determine the volatilization temperature of hydrocarbons in contact with the outside surface of the second tubular member.

In accordance with another specific feature of the invention, insulation extends along the outside of first tubular member for the same fixed distance that the insulation extends for the second tubular member to insure the heat space annular passage between the first and second tubular members is thoroughly insulated thus permitting the water jacket to establish a steady state temperature gradient over the fixed insulation distance.

In accordance with another aspect of the invention, a batch coil annealing furnace is provided in combination with the temperature probe. The batch coil furnace has an inner, removable cover positioned over metal strip wrapped into a coil containing oily surface residues; a removable outer cover positioned over the inner cover; a base upon which the inner and outer covers rest and an exhaust duct in fluid communication with the inner cover for maintaining the atmosphere within the inner cover at a desired pressure. A temperature probe measures the temperature within the inner cover for controlling the firing of burners in the outer cover. The improvement includes the temperature probe having an open ended first tubular member with a burner mounted at one end of the first tubular member and closing that end to which it is mounted so that the burner is adapted to fire its products of combustion through the first tubular member and out the open end thereof. A closed end second tubular member concentrically receives the first tubular member to define an annular heat space therebetween and extends into the exhaust duct. The second tubular member has an exhaust port at its closed end in fluid communication with the annular heat space and the exhaust port is outside the exhaust duct and adjacent to the probe's burner. Insulation extends a fixed distance along the interior of the second tubular member from its first closed end for preventing the burner's products of combustion from directly contacting the second tubular member along the fixed distance over which the insulation extends. A water jacket adjacent the first closed end of the second tubular member receives a cooling fluid for establishing a steady state temperature gradient longitudinally extending along the outside surface of the second tubular member over the fixed distance whereby the temperature at which the oily deposits volatilize from contact with the outside surface of the second tubular member without forming carbon can be ascertained.

In accordance with another specific aspect of the invention, the exhaust duct is provided with a sight port and thermocouples are imbedded into the outside surface of the second tubular member for determining the volatilization temperature of the hydrocarbons as they travel along the outside surface of the second tubular member.

Accordingly, it is a specific object of the invention to provide a batch coil annealing furnace with a temperature probe which permits the batch coil annealing furnace to be initially operated at a preheat temperature which burns off the oily residue on the strip without forming carbon soot.

It is another general object of the invention to provide a temperature probe which establishes a steady state, temperature gradient along a portion of its length which probe can be subjected to any furnace atmosphere to determine the temperature at which the furnace process is to be controlled, such as, for example, sintering of powdered metal parts, pyrolyzing of waste, etc.

It is still yet another feature of the invention to provide a relatively inexpensive device which can be used in high temperature applications as a temperature probe.

Still further objects and features of the invention will become apparent to those skilled in the art upon reading and understanding the Detailed Description Of The Preferred Embodiment set forth below.

BRIEF DESCRIPTION OF THE DRAWINGS

The invention may take form in certain parts and arrangement of parts, a preferred embodiment of which will be described in detail herein and illustrated in the accompanying drawings which form a part hereof and wherein.

DETAILED DESCRIPTION OF THE PREFERRED EMBODIMENT

Figure 1:
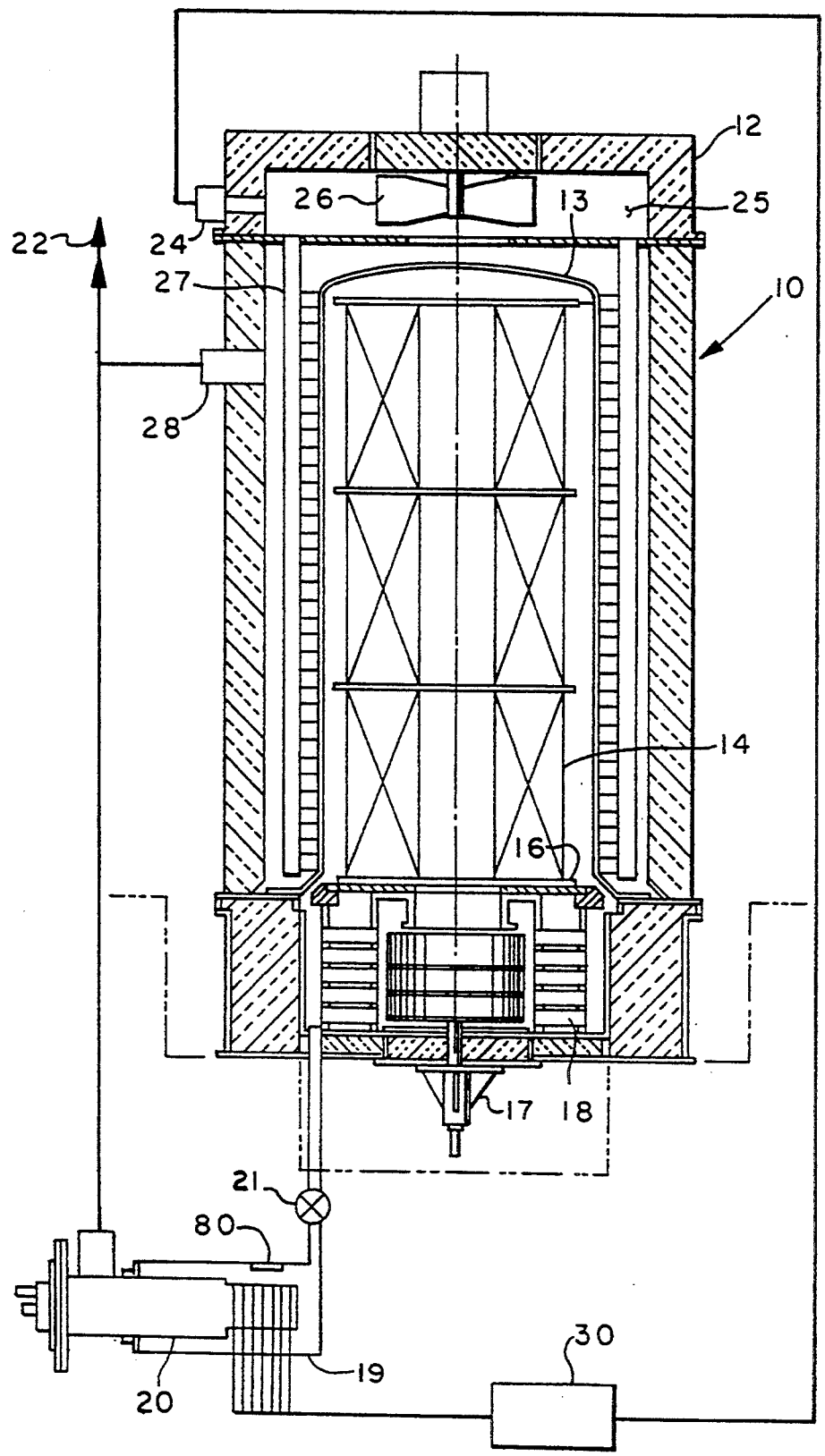
FIG. 1 is a schematic, sectioned view of a batch coil annealing furnace employing the temperature probe of the present invention.

Referring now to the drawings wherein the showings are for the purpose of illustrating a preferred embodiment of the invention only and not for the purpose of limiting the same, there is shown in FIG. 1 a conventional single stand, batch coil annealing furnace which includes a removable outer cover 12 which surrounds or receives therein a removable inner cover 13. Inner cover 13 receives or surrounds metal strip which is wound into coils 14. In the preferred embodiment, there are three coils 14 stacked one on top of the other which are contained within inner cover 13. Outer cover 12, inner cover 13, and metal strip coils 14 rest on an annealing stand or base 16. Base 16 includes a fan 17 and fan diffuser 18 for circulating a furnace atmosphere within inner cover 13 about metal strip coils 14 in a conventional manner. An exhaust duct 19 is in fluid communication with furnace atmosphere within inner cover 13 through base 16 and a valve operated damper 21 in exhaust duct 19 controls the pressure of the furnace atmosphere within inner cover 13 in a conventional manner. Exhaust duct 19 vents to stack (as do all the burners) indicated by reference numeral 22. Inserted within exhaust duct 19 is the temperature probe 20 of the present invention.

Outer cover 12 is equipped with a gas fired burner 24 which heats inner cover 13 which in turn heats the work or metal strip coils 14. In the furnace illustrated, outer cover gas fired burner 24 fires its products of combustion into a plenum chamber 25 which by means of a fan 26 is forced into a plurality of longitudinally extending distributor tubes 27 which have jet orifices formed therein and from which the products of combustion impinge inner cover 13 as jet streams. The orifices are diagrammetrically shown in FIG. 1 as a plurality of straight lines. After impinging and heating inner cover 13, the products of combustion are then exhausted from outer cover 12 through an outer cover exhaust port 28 to stack 22. As thus far described and with the exception of temperature probe 20, batch coil annealing furnace 10 is entirely conventional.

As noted above, when strip is cold rolled, the strip has an oily residue imparted by the rolls of the rolling mill onto its surface. When strip coils 14 are subsequently placed into batch coil annealing furnace 10 and the coils are heated to their annealing temperature, the residual oils are gasified and are exhausted to stack 22. The oils, depending upon the temperature and their composition, are either pyrolyzed, or polymerized. As noted above, the rolling oils are mixtures of petroleum derivatives, mineral oils, animal fats and other additives. Furthermore, solely as a function of the temperature of reaction, it is possible, because the oils are hydrocarbons, to simply produce by heat of reaction, hydrogen and free carbon. As noted above, free carbon in the form of carbon soot can attach itself to the surface of the strip and without discussing carbon impact on the metallurgical qualities of the strip during the annealing process (i.e., decarburization, etc.), the presence of carbon on the surface of the strip adversely impacts subsequent operations in which the strip is coated (i.e., such as zinc) or painted. Because the composition of the residual rolling oils vary, not only from mill to mill, but also within each mill, it is not possible to set one temperature at which batch coil annealing furnace 10 can be operated to burn off the residual oils without forming carbon soot. Thus, conventional practice is to heat metal strip coils 14 to a set temperature, i.e., 1000° F., and hold that temperature for some time with the belief that during this preheat time, the oils are volatilized. For want of a more accurate term, and simply for purposes of definition, the term "volatilize" when used in this specification and in the claims, means the gasifying of a hydrocarbon in a heat reaction which does not produce, or significantly produce, free carbon. The point is that under conventional practice, since the preset temperature for burning off the oily residuals is arbitrarily set, the residual oils are either not completely burned off with the result that during the annealing stage, they are heated to a temperature which produces carbon or, the preset temperature is such that they produce free carbon or carbon sooting during the preheat stage. Accordingly, it is a primary feature of the invention to provide a temperature probe 20 which can determine on a batch by batch basis what the preheat temperature is for the specific coils which are to be annealed so that the residual oils are volatilized, i.e., gasified in a manner so as not to produce or produce significant amounts of free carbon, i.e., carbon soot. Once this temperature is established for the metal strip coils 14 in batch coil annealing furnace 10, a conventional controller 30 can be used to regulate the firing of outer cover gas fired burner 24 and thus control the preheat temperature of the furnace atmosphere within inner cover 13. It should be clear that the preheat temperature may vary from one batch to another.

Figure 2:
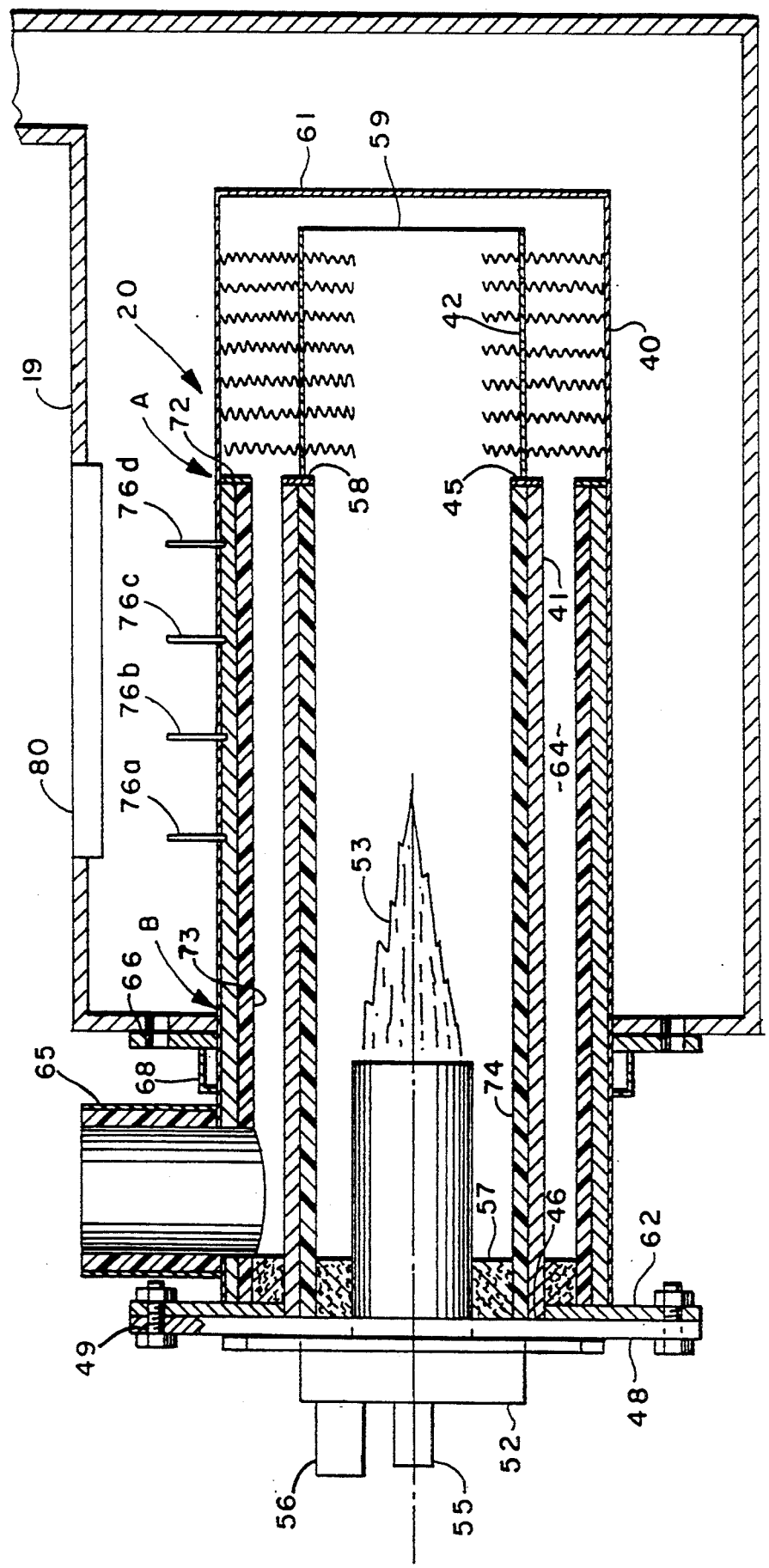
FIG. 2 is a schematic, longitudinally-sectioned view of the temperature probe of the present invention.
Figure 3:
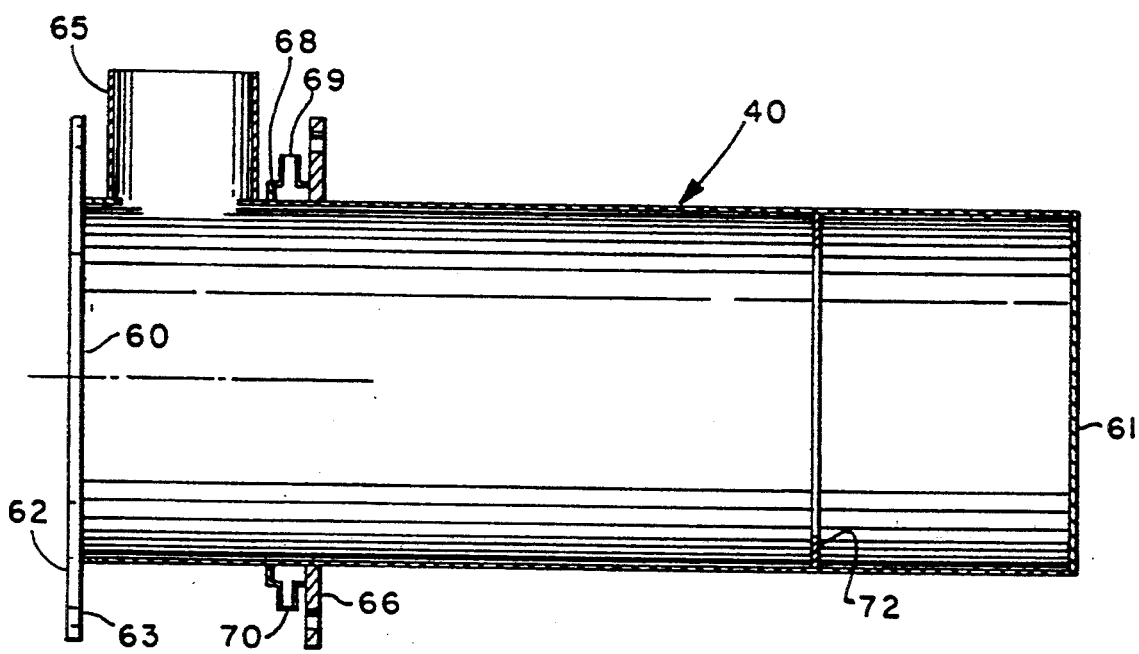
FIG. 3 is a schematic, longitudinal view of the outer tubular member of the temperature probe.
Figure 4:
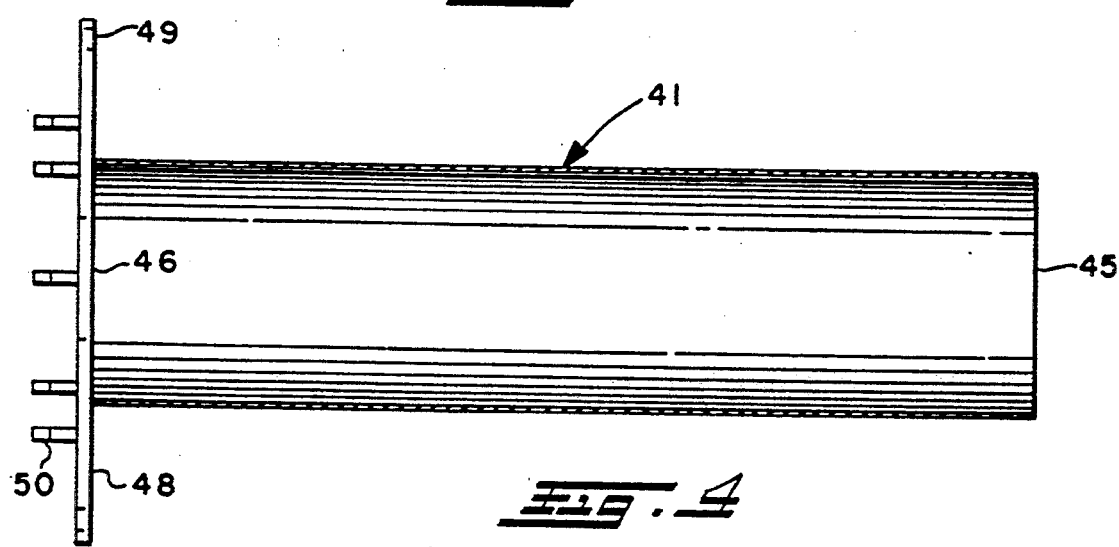
FIG. 4 is a schematic, longitudinal view of the inner tubular member of the present invention.
Figure 5:
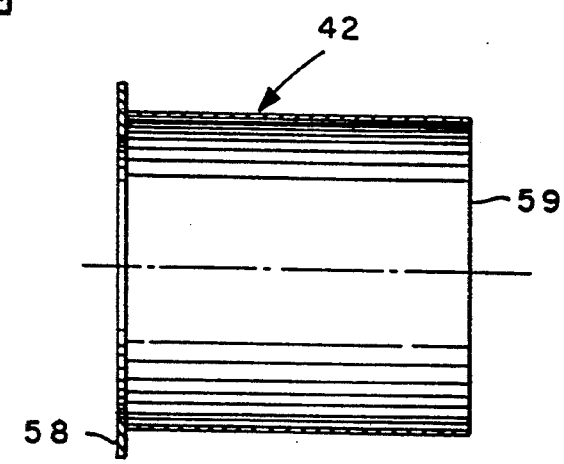
FIG. 5 is a schematic, longitudinal view of the extension for the inner tubular member.

Referring now to FIGS. 2 through 5, there is shown in FIG. 2 the assembled temperature probe 20 of the present invention which includes an outer closed end tubular member 40 (preferably cylindrical) as shown in FIG. 3, which receives an open ended, inner tubular member 41 (preferably cylindrical) as shown in FIG. 4, which in turn has secured to its end a tubular extension 42 as shown in FIG. 5.

Inner tubular member 41 is preferably made of a heat resistant stainless steel of light gauge (about 14 gauge)

and has an open distal end 45 and an open base end 46 to which an annular mounting plate 48 is affixed. Annular mounting plate 48 has a plurality of circumferentially spaced outer mounting holes 49 for securing outer tubular member 40 thereto. Positioned radially inwardly therefrom is a plurality of circumferentially spaced burner studs 50. A gas fired burner 52 is secured to inner tubular member 41 by burner studs 50 and extends into inner tubular member 41 so that the burner's products of combustion indicated by flame front 53 fire down the length of inner tubular member 41 and exit its open distal end 45. As shown in FIG. 2, gas fired burner 52 is provided with a conventional combustion air inlet 55 and a gas inlet 56 and is packed with a suitable burner insulation 57 such as Kaowool about open base end 46 thus making base end 46 a sealed or closed end of inner tubular member 41.

Secured to open distal end 45 of inner tubular member 41 is tubular extension 42 shown in FIG. 5, which is made of a heat resistant stainless steel alloy but of heavier thickness (preferable about ⅛") than inner tubular member 41 since tubular extension 42 is not insulated. In the preferred embodiment, tubular extension 42 is open ended and has an annular open flanged end 58 which is secured to open distal end 45 of inner tubular member 41. The length of tubular extension 42 is sized so that the opposite open end 59 is spaced to be closely adjacent the closed end of outer tubular member 40. In the preferred embodiment, the distance of inner tubular member is about 34.5 inches and the distance of tubular extension 42 is about 8 inches so that tubular extension open end 59 is spaced about 1 inch from the closed end of outer tubular member 40. An alternative construction (not shown) would be to close opposite open end 59 of tubular extension 42 and provide a series of circumferentially spaced exhaust openings at spaced increments along the length of tubular extension 42. The burner products of combustion would then dead end against the now closed end of tubular extension 42 and would be forced out through the exhaust openings to impinge outer tubular member 40 over its end portion. This alternative type of construction would have the effect of assuring that the distal end portion of outer tubular member 40 would be at the burner temperature. However, it has been found in practice that the temperature of outer tubular member over its distal end portion is constant for the tubular extension 42 configuration described for the preferred embodiment. The alternative construction, which should be clear to those skilled in the art from the foregoing description, is simply mentioned should there be an application where an extremely long length probe having a long temperature gradient is desired.

Referring now to FIGS. 2 and 3, outer tubular member 40 has an open base end 60 and an opposite closed end 61. Attached to open base end 60 is an annular mounting plate 62 having a plurality of circumferentially spaced mounting holes 63 by which outer tubular member 40 is secured to inner tubular member 41 as shown in FIG. 2. When assembled, outer tubular member's open base end 60 becomes a sealed or closed end. Also, when assembled a longitudinally-extending, annular heat spaced 64 is formed between inner and outer tubular members 41, 40. Adjacent annular mounting plate 62 is an exhaust port 65 in fluid communication with annular heat space 64 for exhausting the products of combustion emanating from gas fired burner 52. Adjacent exhaust port 65 is an annular mounting collar 66 extending radially outwardly from outer tubular member 40 by which outer tubular member 40 can be secured to exhaust duct 19. Between exhaust port 65 and annular mounting collar 66, there is formed on the outside of outer tubular member 40 an annular cooling water jacket 68 through which a liquid coolant is circulated from an inlet 69 to a diametrically opposed outlet 70.

Secured to the inside of outer tubular member 40 at a distance approximately equal to or aligned with open distal end 45 of inner tubular member 41 is an annular insulation stop ring 72. Extending for a fixed distance between open base end 60 and insulation stop ring 72 is a layer of conventional, outer tubular member ceramic furnace fibrous insulation 73. Similarly, secured to the outside (or alternatively, the inside) of inner tubular member 41 from open base end 46 to annular open flange end 58 of tubular extension 42 is likewise a layer of conventional, inner tubular member ceramic furnace fibrous insulation 74. Outer tubular member ceramic furnace fibrous insulation 73 and inner tubular member ceramic fibrous insulation 74 is a vacuum-formed ceramic insulation of a relatively high density, such as 10–15 lb/ft.$^3$ and its surface is sprayed with a conventional silica sand mixture such as Kaowool rigidizer, to make it hard and rigid. Again, insulation 73, 74 is conventional and well known in the furnace art. Insulation 73, 74 make heat space 64 insulated over the fixed length thereof so that a temperature gradient can be established.

Positioned on the outside surface of outer tubular member 40 over the distance spanned by outer tubular member ceramic furnace fibrous insulation 73 is a temperature indicating or temperature indicia markings. In its broad form, the temperature indicia markings could simply be lines at which temperature crayon sticks could be used to determine temperature corresponding to the lines. In the preferred embodiment, the temperature markings take the form of thermocouples 76 embedded into the outside surface of outer tubular member 40 at longitudinally spaced increments. In the preferred embodiment, there are four thermocouples designated 76a, 76b, 76c, and 76d.

In operation, gas fired burner 52 fires its products of combustion down inner tubular member 41 through tubular extension 42 and out opposite open end 59 of tubular extension 42. The products of combustion dead end against closed end 61 of outer tubular member 40 and travel within the insulated annular heat space 64 formed between inner tubular member 41 and outer tubular member 40 to exhaust port 65 where products of combustion are vented to stack 22. Because of the insulation, the temperature of the hot products of combustion within annular heat space 64 remain constant or uniform throughout the length of annular heat space 64. This is important because it assures a uniform temperature gradient. The uninsulated portion of outer tubular member 40 which overlies tubular extension 42 is at the temperature of the products of combustion of gas fired burner 52. Typically, this is at about 1500° F. However, the outside surface temperature of outer tubular member 40 adjacent annular cooling water jacket 68 is at about a temperature of 150° F. The presence of outer tubular member ceramic furnace fibrous insulation 73 in combination with the presence of inner tubular member ceramic fibrous insulation 74 provide a very effective insulated shield which permits the temperature of outer tubular member to gradually decrease along the fixed length of insulation. This is shown in FIG. 2 as extending from point A, which is at a high temperature of about 1500° F. to point B which is a low temperature of about 150° F. Significantly, because of the geometry of the probe coupled with the insulation of both inner and outer tubular members 41, 40, the temperature gradient established along the length of outer tubular member 40 is almost linear. More importantly, the temperature gradient is uniform or steady state.

It is known that at temperatures of about at 1500° F. hydrocarbons will decompose and form free carbon. Thus, by simply providing a sight port 80 in exhaust duct 19, one can see (because of the temperature gradient existing along the length of outer tubular member 41) where carbon soot forms on temperature probe 20 and likewise, one can see where an oily residue appears on the surface of outer tubular member 40. By operating the furnace at a preheat temperature where carbon is not formed on temperature probe 20, one can be assured that free carbon will not form within batch coil annealing furnace 10 during preheat. Also, by operating the furnace at a temperature above the band where oily deposits are formed on the outside surface of outer tubular member 40, one can be assured that the oily residues are volatilized. Thermocouples 76 can indicate precisely what the temperatures of the atmosphere within the inner cover as it travels along the outside surface of the outer tubular member 40 are which can then be automatically set by controller 30, although, an optical pyrometer could likewise be used to determine the desired preheat temperature.

Cold rolled steel and strip is covered with a thin film of rolling oil residues which is not removed in the final cleaning operation before recoiling. Rolling mills find it difficult to remove this residual film with existing equipment and existing cleaning methods. These residues polymerize, pyrolize, and form soot or carbon on the steel surfaces. Such surface fouling results in poor paint adherence and is, therefore, very undesirable for applications where a paint or other coating is part of the final product.

Rolling oils are mixtures of petroleum derivatives, mineral oils, animal fats, and other additives. Determination of one boiling point, or one sooting temperature, or one coking temperature is, therefore, not possible.

To overcome the lack of an industry determination procedure for the sooting temperature a probe has been designed that will give a good indication of the temperature range at which it is safe to expose rolling oil vapors to steel surfaces without formation of carbon deposits. This same probe will also clearly indicate at which temperatures solid carbon will begin to form.

The probe consists of a tubular vessel which is heated on its distant end which is closed. On its other end a burner is located that produces hot flue products. The hot flue products are directed against a short cylindrical section at the distant end and the external surface of the tubular member is heated to a high temperature in the range of 1500° F. at which temperature it is known that carbon formation will occur. The tubular member is insulated from the flue gases in the intermediate section and is connected to a water cooled flange located close to the burner. The external surface of the tubular member will, therefore, assume the entire continuum of temperatures between approximately 1500° F. and 150° F. By maintaining these temperatures on the same levels over a period of time oil vapor will either condense, will not deposit, will polymerize, will pyrolize, or will deposit soot along the length of the external surface of the tubular member. By knowing the steady state temperature of the surface and by visual inspection of the surface condition it is now possible to relate thermal oil deposit and decomposition behaviors with the temperature ranges at which they occur.

The invention has been described with reference to a preferred embodiment. Obviously, alterations and modifications will occur to those skilled in the art upon reading and understanding the invention. More specifically, while the invention has been developed for the specific purpose of volatilizing oily residue without forming carbon soot, other applications of temperature probe 20 should be apparent to those skilled in the art. For example, in either sintering or powder metallurgy processing, the rate at which the resins are volatilized by heat to form certain bonds in the work, may have to be controlled. The temperature probe of the present invention could effect such control. Further, in the pyrolyzing of certain waste, hydrocarbons may likewise be emitted and to satisfy clean air standards, such as those governing $NO_x$, it may be desirable to assure that the hydrocarbons are not immediately gasified into hydrogen and carbon. The temperature probe could be applicable to such installations. Thus, in its broad sense, the temperature probe is applicable to any application where a measuring device having an externally formed, steady state temperature gradient is to be inserted into a gaseous atmosphere to determine the temperature at which the gaseous atmosphere is to be controlled. It is intended to include all such modifications and alternations insofar as they come within the scope of the present invention.

Having thus defined the invention it is claimed:

1. A temperature probe comprising:
   a. an open ended first tubular member;
   b. a burner mounted at one end of said first tubular member and closing said one end thereof, said burner adapted to fire its products of combustion though said first tubular member and out the opposite open end thereof:
   c. a second tubular member having its first and second ends closed concentrically receiving said first tubular member and defining a longitudinally-extending annular heat space therebetween, said second tubular member having an exhaust port at its first closed end adjacent said burner and in fluid communication with said heat space, said second tubular member having temperature measuring means associated with it;
   d. insulation means extending a fixed distance along the inside of said second tubular member from said first closed end for preventing the burner's products of combustion from directly contacting said second tubular member along said fixed distance; and
   e. water jacket means adjacent said first closed end of said second tubular member receiving a cooling fluid for establishing a steady state temperature gradient on the outside of said second tubular member over said fixed distance.

2. The probe of claim 1 wherein said insulation means also extends said fixed distance along the outside of said first tubular member whereby said annular heat space is insulated, 3. The probe of claim 1 wherein said insulation means includes conventional fibrous insulation, 4. The probe of claim 3 further including a mounting flange extending from said second tubular member, said water jacket means includes a water jacket formed on the outside of said second tubular member between said exhaust port and said mounting flange.

5. A batch coil annealing furnace in combination with a temperature probe, said batch coil furnace having a removable inner cover positioned over metal strip containing oily residues which is wrapped into a coil, a removable outer cover positioned over said inner cover, a base upon which said covers rest, an exhaust duct in fluid communication with said inner cover for maintaining the atmosphere within said inner cover at a desired pressure, and a temperature probe for measuring the temperature of said atmosphere within said inner cover, the improvement comprising:

said temperature probe having:
- a. an open ended first tubular member;
- b. a burner mounted at one end of said first tubular member and closing said one end thereof, said burner adapted to fire its products of combustion through said first tubular member and out the open end thereof;
- c. a second tubular member having its first and second ends closed concentrically receiving said first tubular member to define an annular heat space therebetween and said second tubular member extending into said exhaust duct, said second tubular member having an exhaust port in fluid communication with said annular heat space at its first closed end;
- d. insulating means extending a fixed longitudinal distance along the inside of said second tubular member from said first closed end for preventing the burner's product of combustion from directly contacting said second tubular member along said fixed distance;
- e. water jacket means adjacent said first closed end of said second tubular member receiving a cooling fluid for establishing a steady state temperature gradient on the outside of said second tubular member over said fixed distance; and
- f. temperature measuring means mounted on said second tubular member for measuring the temperature of the atmosphere within said inner cover as it travels along the outside of said second tubular member.

6. The improvement of claim 5 wherein said insulating means also extends said fixed distance along the outside of said first tubular member whereby said annular heat space is insulated.

7. The improvement of claim 6 wherein said insulating means includes conventional fibrous insulation.

8. The improvement of claim 7 further including a mounting flange extending from said second tubular member, said water jacket means includes a water jacket formed on the outside of said second tubular member between said exhaust port and said mounting flange.

9. The improvement of claim 8 wherein said exhaust duct includes a sight port, said temperature measuring means comprising indicia markings on the outside thereof at fixed longitudinal increments for indicating the temperature at which the inner cover should be maintained at for volatilizing the oily deposits from the steel coils therein.

10. The improvement of claim 9 wherein said temperature measuring means further comprises thermocouples imbedded in the outside surface of said second tubular member at said markings for recording the temperature thereof.

11. The improvement of claim 10 wherein said burner means produces a temperature of about 1500° F. at the outside surface of said second tubular member at said second closed end while said water jacket means produces a temperature of about 150° F. at the outside surface of said second tubular member adjacent said first closed end.

* * * * *